US006494576B1

(12) United States Patent
L'Esperance, Jr.

(10) Patent No.: US 6,494,576 B1
(45) Date of Patent: Dec. 17, 2002

(54) METHOD AND APPARATUS FOR SPECTROPHOTOMETRY OF THE EYE

(76) Inventor: Francis A. L'Esperance, Jr., 255 Oakwood Rd., Englewood, NJ (US) 07631

( * ) Notice: Subject to any disclaimer, the term of this patent is extended or adjusted under 35 U.S.C. 154(b) by 112 days.

(21) Appl. No.: 09/676,387

(22) Filed: Sep. 29, 2000

Related U.S. Application Data

(60) Provisional application No. 60/156,707, filed on Sep. 30, 1999.

(51) Int. Cl.$^7$ .................................................. A61B 3/14

(52) U.S. Cl. ....................................................... 351/206

(58) Field of Search ................................. 351/205, 206, 351/207, 211, 221; 600/109; 250/234; 356/300, 302, 303

(56) References Cited

U.S. PATENT DOCUMENTS

| 4,877,322 A | 10/1989 | Hill |
| 5,282,464 A | 2/1994 | Brain ..................... 128/207.15 |
| 5,318,022 A | 6/1994 | Taboada et al. |
| 5,582,168 A | 12/1996 | Samuels et al. |
| 6,255,646 B1 * | 7/2001 | Shimada ..................... 250/234 |
| 6,276,798 B1 * | 8/2001 | Gil et al. ..................... 351/206 |

FOREIGN PATENT DOCUMENTS

| DE | 4414679 A1 | 11/1995 |
| DE | 19538372 A1 | 4/1997 |
| EP | 0589191 A1 | 3/1994 |
| EP | 0776628 A2 | 6/1997 |
| EP | 0792619 A1 | 9/1997 |
| WO | WO93/07801 A | 4/1993 |
| WO | WO00/02479 A | 1/2000 |
| WO | WO02/26119 A2 | 4/2002 |

OTHER PUBLICATIONS

Brown, et al., "Noninvasive Oxygen Monitoring" *Critical Care Clinics*, vol. 4(3), Jul. 1988, pp. 493 to 509.
Mahadevan–Jansen, et al., "Near–Infrared Raman Spectroscopy for In Vitro Detection of Cervical Precancers" *Photochemistry and Photobiology*, vol. 68(1), 1998, pp. 123 to 132.
Mainster, "Laser Light, Interactions, and Clinical Systems" in L'Esperance, Jr., editor, *Ophthalmic Lasers* (Third Edition, vol. I), The C.V. Mosby Company, 1989, pp. 61 to 77.
Small, et al., "Strategies for Coupling Digital Filtering with Partial Least–Squares Regression: Application to the Determination of Glucose in Plasma by Fourier Transform Near–Infrared Spectroscopy", *Analytical Chemistry*, vol. 65, No. 22, 1993, pp. 3279 to 3289.
Ohmeda Inc., The BOC Group, "Biox 3700/3700e Pulse Oximeter Operator's Manual", 1988, 1996.
Bibliography, "Pulse Oximeter Measurements", Nerac.com (Sep. 26, 2000).
Bibliography, "Pulse Oximeter Reviews", Nerac.com (Sep. 26, 2000).
U.S. Provisional Application No. 60/101,893, filed Sep. 25, 1998, "Photographic Retinal Oximetry", Francis A. L'Esperance including Filing Receipt, Cover Sheet, Specification, and Drawings.
Schoenberger, Chana R., "Needless Needles, Diagnosing disease without taking blood, once a fringe idea, is close to reality.", Forbes magazine, Oct. 15, 2001, p. 114.
Woolley, Scott, "Spotting Evil, New technology may well be able to pick terrorists out in a crowd and create a record of their movements–and yours, too.", Forbes magazine, Oct. 15, 2001, p. 46 to 48.

(List continued on next page.)

*Primary Examiner*—George Manuel
(74) *Attorney, Agent, or Firm*—Morgan, Lewis & Bockius LLP

(57) ABSTRACT

A method and apparatus for spectrophotometry for non-invasively measuring the chemistry of the blood in the eye.

32 Claims, 13 Drawing Sheets

OTHER PUBLICATIONS

"Topcon, Retinal Camera TRC–50EX", Topcon Corporation, 1998, 8 pages.

"Topcon, Retinal Camera TRC–50FX", Topcon Corporation, 1999, 4 pages.

"Topcon, IMAGEnet™2000 Digital Imaging Systems, Up–to–the–Minute, State–of–the–Art", Topcon Corporation, Jul. 1999, 4 pages.

"Topcon, Retinal Camera TRC–502X", Topcon Corporation, 1999–2000, 8 pages.

"Topcon, Non–Mydriatic Retinal Camera TRC–NW6", Topcon Corporation, 2000, 4 pages.

"Topcon, Non–Mydriatic Retinal Camera TRC–NW6S/NW6SF", Topcon Corporation, 2000, 6 pages.

"Topcon, IMAGEnet™2000, Topcon and IMAGEnet™2000 make the difference . . . and here's why . . . Features", Topcon America Corporation, 2000, 1 page.

"Topcon, IMAGEnet™2000, IMAGEnet™ and Stereo Imaging", Topcon America Corporation, 2000, 1 page.

"IMAGEnet™2000 Digital Imaging Systems, IMAGEnet PDT Rings for Photo Dynamic Therapy Applications", Topcon, 1 page.

Kock, et al., "Reflectance Pulse Oximetry Measurements from the Retinal Fundus", IEEE Transactions on Biomedical Engineering, Aug. 1993, pp. 817 to 823, No. 8, IEEE, New York.

PCT International Search Report and PCT Notification of Transmittal thereof for International Application No. PCT/US01/30240, mailed Apr. 23, 2002, Form PCT/ISA/210 (first sheet with continuation, (continued next) Jul. 1998, second sheet with continuation, Jul. 1992, patent family annex, Jul. 1992). Form PCT/ISA/220 (Jul. 1998, Notes to Form PCT/ISA/220, first and second sheets, Jan. 1994).

* cited by examiner

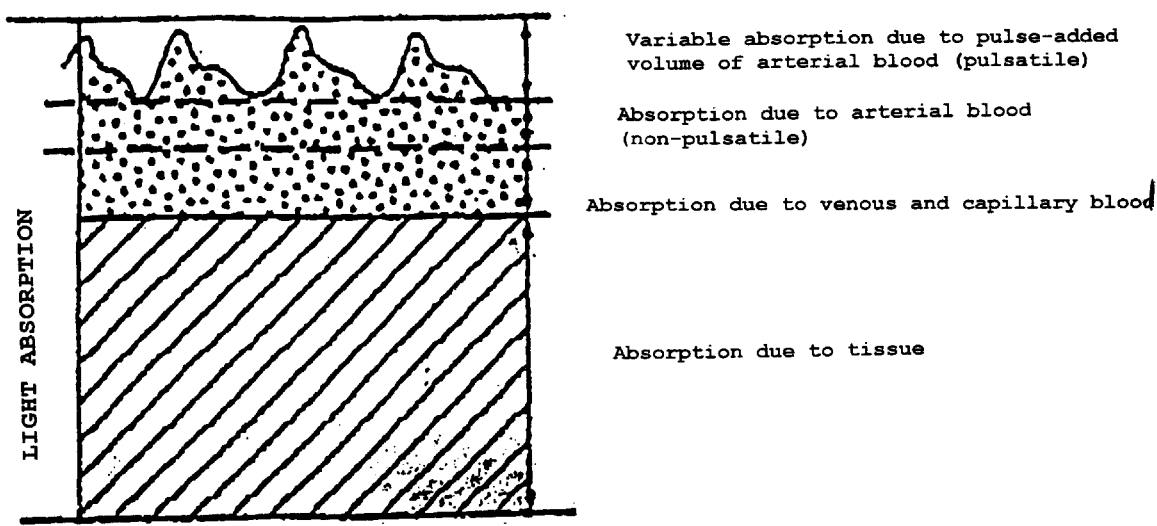
Figure 3.: Tissue composite showing dynamic and static components that affect light absorption during pulse oximetry. (Adapted from Ohmeda 3700. Pulse Oximeter Users Manual. Madison, WI, Ohmeda, 1989, p22. Provided by Ohmeda, Inc. The BOC Group)

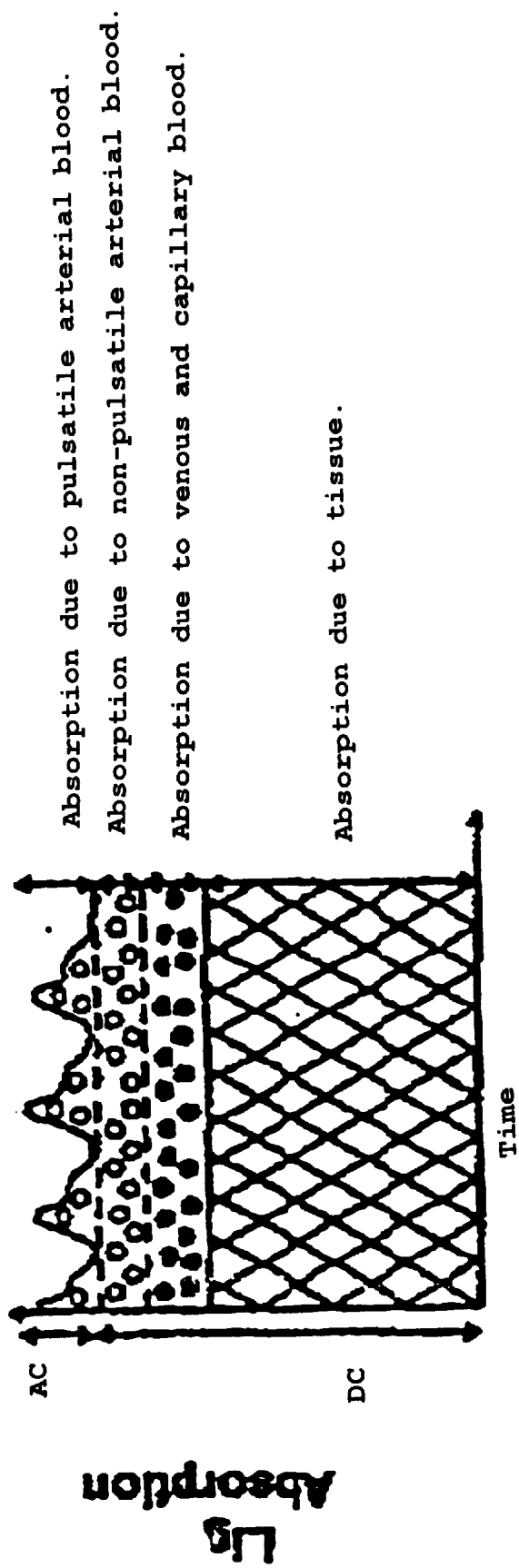
Figure 4.: Schematic representation of the absorption of light by living tissues. Note that arterial blood (the ac component) is the only pulsatile component in the series of light absorbers in living tissues. The dc component represents all of the nonpulsatile absorbers. (Adapted from Ohmeda Pulse oximeter model 3700 Service Manual)

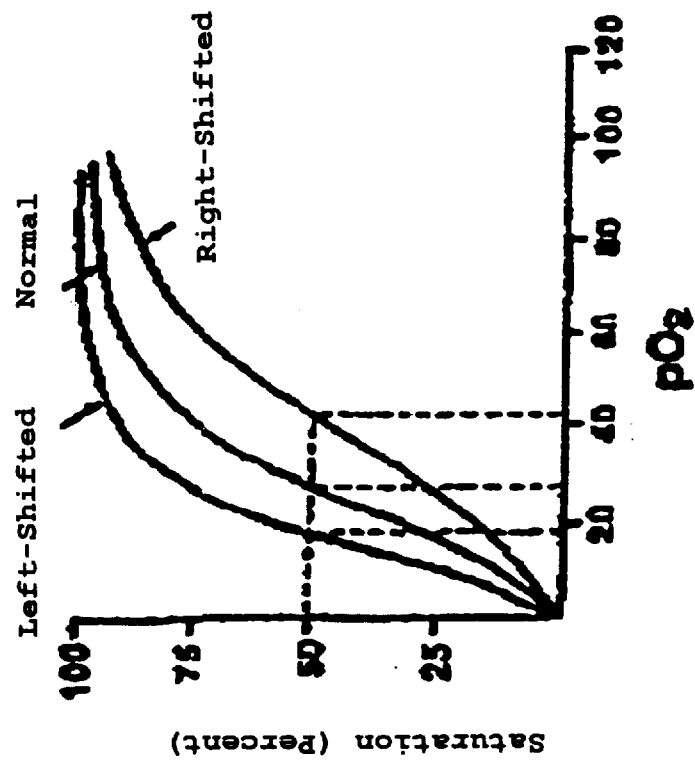

Figure 5: The oxyhemoglobin dissociation curve. The relationship between arterial saturation of hemoglobin and oxygen tension is represented by the sigmoid-shaped oxyhemoglobin dissociation curve. When the curve is left-shifted, the hemoglobin molecule binds oxygen more tightly. (Reproduced from Brown M. Vender JS: Non-invasive oxygen monitoring. Crit Care Clin 4:495, 1988.

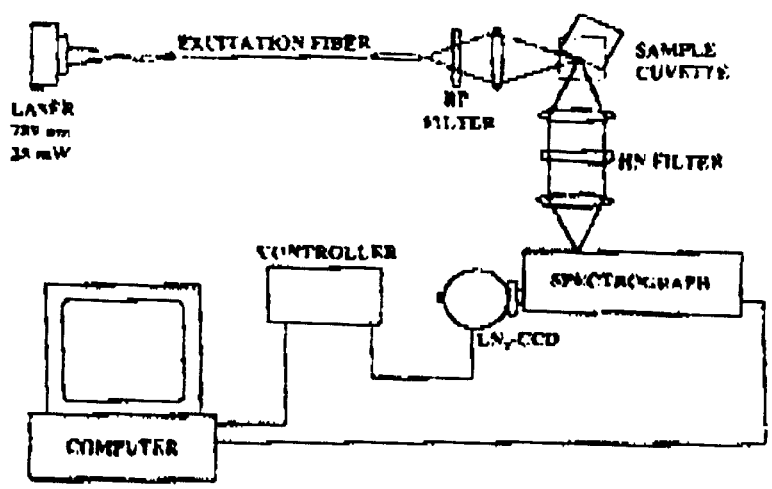
Figure 6. Experimental setup used to measure NIR Raman spectra

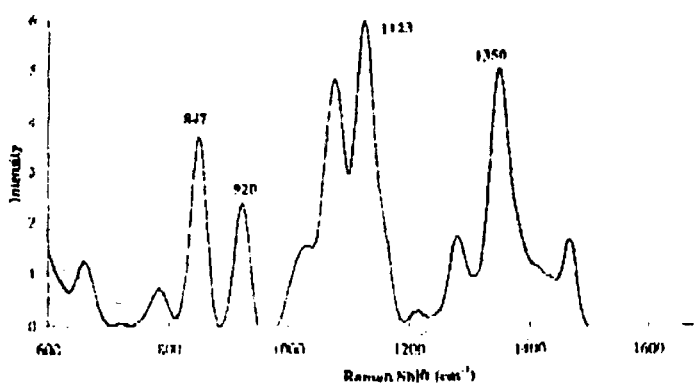
Figure 7. Raman spectrum of a dilute solution of glucose.

Table II. Description of Data Sets Used in Calibration and Prediction

| source | calibration[*] | | prediction | |
|---|---|---|---|---|
| | samples | spectra | smaples | spectra |
| lot I | 16 (4) | 100 (25) | 3 | 13 |
| lot II | 20 (6) | 103 (28) | 5 | 30 |
| lot III | 19 (4) | 97 (17) | 6 | 26 |
| total | 55 (14) | 300 (70) | 14 | 69 |

[*] Samples and spectra comprising the monitoring set for the filter generation work are indicated in parentheses.

Figure 8.

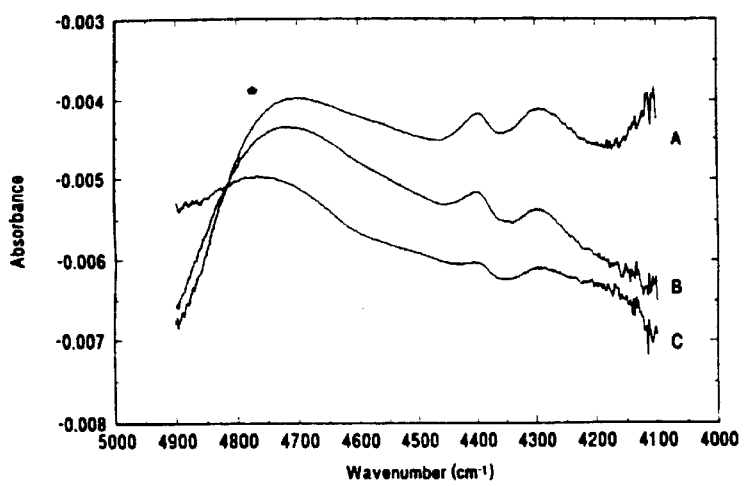
Figure 9. Absorbance difference spectra of three plasma samples. Spectra A-C correspond to samples 67 (15.2 mM), 61 (12.8 mM), and 57 (9.1 mM), respectively. Glucose bands are observed in the regions of 4300, 4400, and 4700 $cm^{-1}$.

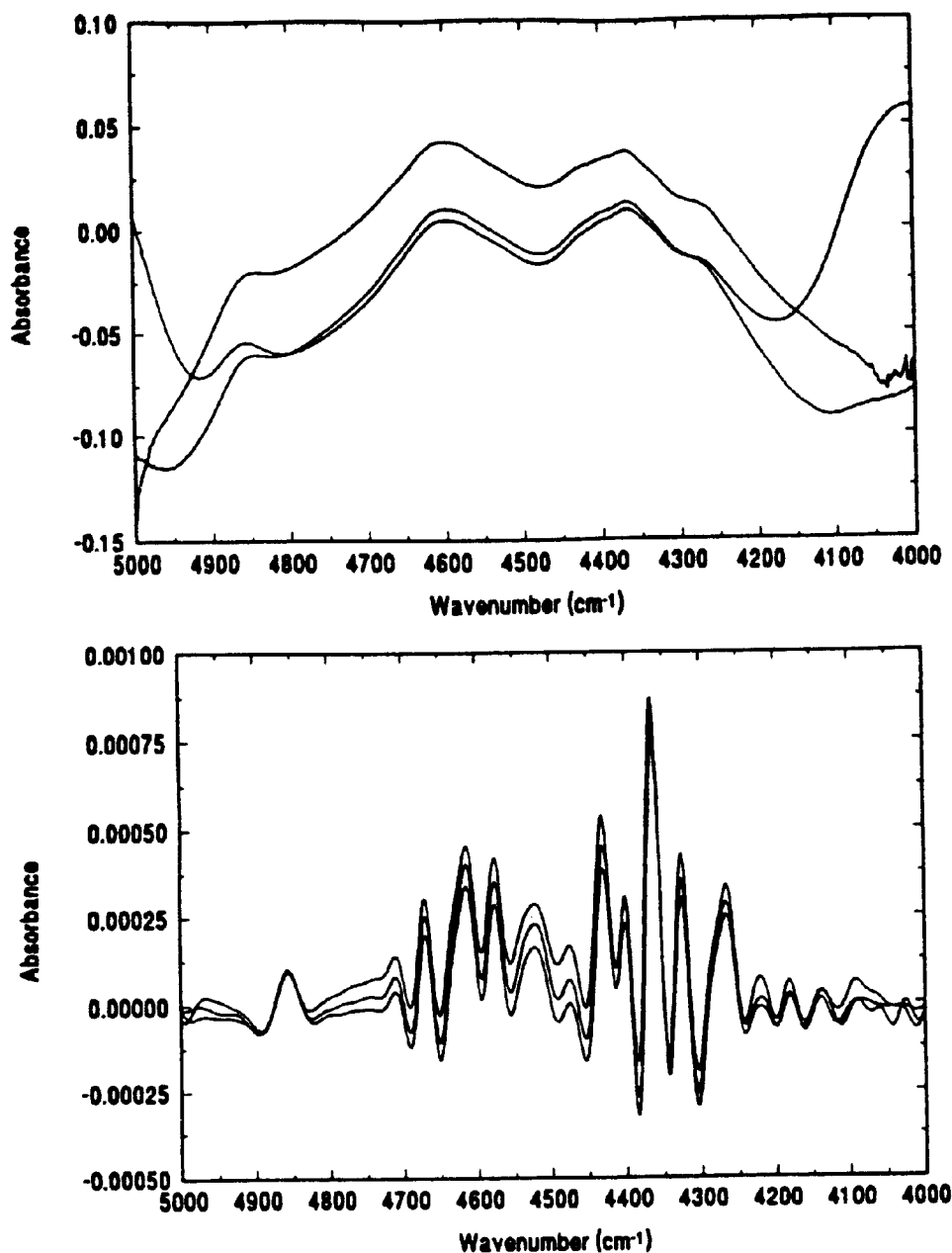

(Top) Absorbance spectra of two replicates of sample 4 (10.8 mM) and one replicate of sample 58 (10.9 mM). (Bottom) Corresponding spectra after Fourier filtering with a Gaussian bandpass function centered at 0.052$f$ and with a width specified by a standard deviation of 0.013$f$. Note the decrease in baseline variation and the enhancement of the spectra in the region of the glucose bands at 4400 and 4300 cm$^{-1}$.

Figure 10

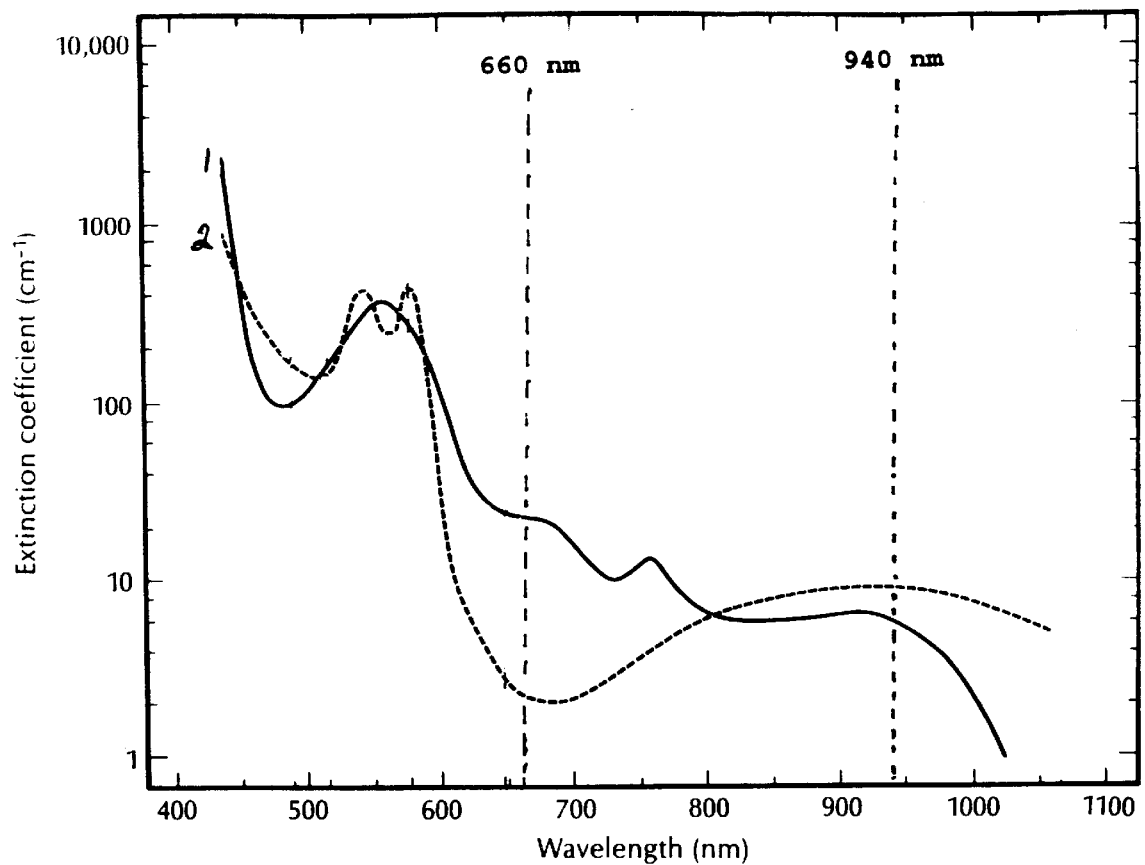
Figure 11. Extinction coefficient versus wavelength for reduced hemoglobin (*curve 1*), and oxygenated hemoglobin (*curve 2*).

METHOD AND APPARATUS FOR SPECTROPHOTOMETRY OF THE EYE

This application claims the benefit of U.S. Provisional Application No. 60/156,707, filed Sep. 30, 1999, the entire disclosure of which is hereby incorporated by reference herein.

BRIEF STATEMENT OF THE INVENTION

This invention relates to the use of spectrophotometric absorption for non-invasively measuring the chemistry of the blood in the eye.

BACKGROUND OF THE INVENTION

Photographic retinal oximetry, like pulse oximetry, computes arterial $O_2$ saturation by using variations in the absorption of light in the red and IR (infrared) wavelengths caused by the pulsation of arterial blood. Arterial oxygen saturation of the blood as determined by a photographic retinal oximeter is designated $SpO_2$ (and is shown in FIG. 3). Increased arterial blood flow during systole expands tissue beds by delivering additional blood with each pulse. When a pulse of light is shone onto a blood-perfused tissue bed, each of the arterial pulsations alters the amount of light transmitted through and reflected back from the tissue bed. By working only with the variations in the light caused by the pulsing of the tissue bed, a photographic retinal oximeter can be operated in a fashion to ignore light absorption by nonpulsatile elements in the light transmission pathway (e.g., choroid, retina, lens and cornea). This type of analysis is called transmission (or reflectance) oximetry and it uses light at wavelengths of 660 nm (red light, primarily absorbed by reduced hemoglobin) and 910 or 940 nm (infra-red light, primarily absorbed by oxyhemoglobin).

More recent developments in techniques for non-invasive analysis of patients by using light have enabled the use of reflectance oximetry (as opposed to the transmission oximetry just discussed). This newer technique monitors $SpO_2$ (partial pressure of oxygen in the blood) by measuring light reflected from perfused tissues. This approach could be dangerous for additional monitoring capabilities and comparison with the values obtained by transmission oximetry.

Oximetry describes various spectrophotometric techniques that determine the $HbO_2$ saturation (i.e., saturation of hemoglobin with oxygen). If blood exposed to light of a particular wavelength and intensity, measurement of the light absorbed by the oxygenated hemoglobin moiety (whether partially or fully oxygenated) is proportional to the relative amount of $HbO_2$ present. This relationship can be expressed mathematically by A=alc (Equation 1), where A is the amount of light absorbed, a is the absorption of $HbO_2$ at a given wavelength, l is the length of the light path, and c is the concentration of $HbO_2$. Rearranging Equation 1 gives the following mathematic relationship for absorption: a=A/lc (Equation 2). A calibration constant can be derived by comparison of absorption between two substances with identical absorption at a given wavelength (e.g., a standard (st) and an unknown (u) from the equality: $(A/lc)_{st}=(A/lc)_u$ (Equation 3). If the light path length is held constant, the concentration of the unknown substance is determined by the relationship: $c_u=A_u\times c_{st}/A_{st}$ (Equation 4).

Application of these principles to patient monitoring assumes that the measured change in absorption is a function having as its predominant parameter the different forms of hemoglobin present in the blood. The presence of other substances with spectral activity in the light wavelengths used for analyzing biological fluids and molecules will likely result in erroneous measurements (to some degree). Two applications of these principles are routinely used in the clinical management of anesthetized and critically ill patients.

Pulse oximeteres are dual-wavelength spectrophotometers that use a light-emitting diode as a light source and a photodiode as a light detector. The source and detector are usually incorporated into a digital clip that is applied "clothes-pin" fashion to the end of a finger. When the light source and detector are separated by the pulsating arterial vascular bed at the end of the finger, the degree of change in the transmitted light (light emitted minus light absorbed) is proportional to the size of the arterial pulse, the wavelengths of light, and the $HbO_2$ concentration. If the pulse is considered to be entirely due to the passage of arterial blood and the appropriate light wavelengths (e.g., 660 nm and 940 nm) are used, the $SpO_2$ can be continuously measured. The clinical accuracy of pulse oximeters is excellent for $HbO_2$ saturations$\geq 80\%$ when compared with laboratory co-oximeters. At lower oxyhemoglobin concentrations, agreement between the pulse oximeter and the co-oximeter is diminished. Nevertheless, the pulse oximeter still reliably trends the changes in $HbO_2$ saturation.

Fiberoptic techniques allow flow-directed pulmonary artery catheters to measure continuously the $HbO_2$ concentration of mixed venous blood in the pulmonary artery. Mixed venous oximetry is an application of reflectance spectrophotometry, in which light of appropriate wavelengths is flashed down a fiberoptic path; the resultant reflected light from the hemoglobin passes back up the fiberoptic path. The ratio of reflected light between (or among) the different wavelengths is proportional to the mixed venous $HbO_2$ saturation ($SvO_2$). The fiberoptic catheter must be calibrated for reading during use for this technique to provide accurate results. Stability of the calibration is unaffected by temperature variations or by hemoglobin concentration, provided the subject's hematocrit is at least 40%. Another source of error, calibration curves can shifted by 1% for every 0.1 change in the pH of the subject's blood. Thus, calibration against (i) a standard sample of known $HbO_2$, (ii) saturation before insertion, or (iii) a measured $SvO_2$ obtained from a blood sample taken after catheter placement, is feasible and reliable (and desirable). Mixed venous fiberoptic oximetry results correlate well with co-oximetric measurement of $SvO_2$. Clinically acceptable accuracy of these techniques is unaffected by body temperature, hemoglobin concentration, cardiac index, or method of calibration.

Noninvasive oximeters typically measure red and infrared light transmitted through and/or reflected by a tissue bed. Accurate estimation of $SaO_2$ (arterial oxygen saturation) using this method encounters several technical problems. First, there are many light absorbers in the path of transmitted light other than arterial hemoglobin (e.g., cornea, lens, and vitreous and venous and capillary blood). The photographic retinal oximeter takes into account the effect of absorption of light by these tissues and venous blood by assuming that only arterial blood pulsates. FIG. 4 illustrates schematically the series of absorbers in a typical sample of living tissue. At the top of FIG. 4 is the "ac" (pulsatile) component, which represents absorption of light by the pulsating arterial blood in the choroid and retina. The "dc" (baseline) component represents absorption of light by the tissue bed, including venous, capillary, and nonpulsatile arterial blood. The pulsatile expansion of the arteriolar bed increases the path length, thereby increases absorbance.

Pulse oximeters use only two wavelengths of light:; 660 nm (red light) and 940 nm (near-infrared light). The photographic retinal oximeter first determines the ac component of absorbance at each wavelength and then divides this value by the corresponding dc component to obtain a "pulse-added" absorbance that is independent of the intensity of incident light, both ac and dc values determined photographically at the peak or crest (ac) and trough (dc) of the arterial pulse. The oximeter then calculates the ratio R of these pulse-added absorbance, which is empirically related to $SaO_2$ by the formula R ($ac_{660}/dc_{660}$) ($ac_{940}/dc_{940}$) (Eq. 5).

It was a fortuitous coincidence of technology and physiology that allowed the development of solid-state pulse oximeter sensors. Light-emitting diodes are available over a relatively narrow range of the electromagnetic spectrum. Among the available wavelengths are some that not only pass through the skin but also are absorbed by both oxyhemoglobin and reduced hemoglobin. For best sensitivity, the difference between the ratios of the absorbance of $HbO_2$, and Hb at the two wavelengths should be maximized. At a wavelength of 660 nm, reduced hemoglobin absorbs approximately 10 times as much light as does oxyhemoglobin. At the infrared wavelength of 940 nm, the absorption coefficient of oxyhemoglobin (oxygenated hemoglobin) is greater than that of reduced hemoglobin.

SUMMARY OF THE INVENTION

Photographic Retinal Oximetry (PRO) could become the standard of care for monitoring chorio-retinal oxygenation just as pulse oximeters do with digital clips during anesthesia. Photographic Retinal Oximetry (PROs) measure pulse rate and oxygen saturation of hemoglobin ($SpO_2$) noninvasively. FIG. 5 displays the oxyhemoglobin dissociation curve that defines the relationship of hemoglobin saturation and oxygen tension. On the steep part of the curve a predictable correlation exists between $SaO_2$ and $PO_2$. In this steep part of the curve, the $SaO_2$ is a good reflection of the extent of hypoxemia and the changing status of arterial oxygenation. Shifts in the oxyhemoglobin dissociation curve to the right or to the left define changes in the affinity of hemoglobin for oxygen. At a $PO_2$, of greater than about 75 mm Hg., the SaO plateaus and loses its ability to reflect changes in $PaO_2$.

Photographic Retinal Oximetry and Pulse Oximetry are based on several premises:

1. The color of blood is a function of oxygen saturation.
2. The change in color results from the optical properties of hemoglobin and its interaction with oxygen.
3. The ratio of oxygenated ($O_2Hb$) and reduced hemoglobin (Hb) can be determined by absorption spectrophotometry.

Photographic Retinal Oximetry combines the technologies of plethysmography and spectrophotometry. Plethysmography produces a pulse trace that is helpful in tracking circulation. Oxygen saturation can be determined spectrophotometrically based upon the Beer-Lambert law: at a constant flash intensity and hemoglobin concentration, the intensity of light transmitted through the transparent ocular media (cornea, lens vitreous) and the retina and choroid of the mammalian eye is a logarithmic function of the oxygen saturation of hemoglobin. Two wavelengths of light are required to distinguish $O_2Hb$ from reduced Hb. Light-emitting diodes in the pulse sensor emit red (660 nm) and near infrared (940 nm) light. The percentage of each of $O_2Hb$ and reduced Hb is determined by measuring the ratio of infrared and red light sensed by a photodetector. Pulse oximeters perform a plethysmographic analysis to differentiate the pulsatile "arterial" Hb saturation from the nonpulsatile signal resulting from absorption by "venous" blood and by other tissues such as skin, muscle, and bone. The absence of a pulsatile waveform during extreme hypothermia or hypoperfusion limits the ability of a photographic retinal oximeter to calculate the $SpO_2$ under these conditions.

The $SpO_2$, measured by photographic retinal oximetry is not the same as the arterial saturation ($SaO_2$) measured by a laboratory co-oximeter. Photographic retinal oximetry measures the "functional" saturation, which is defined by the equation: Functional $SaO_2=[O_2Hb \div (O_2Hb+reduced\ Hb)] \times 100$. Laboratory co-oximeters use multiple wavelengths to distinguish other types of Hb by their characteristic absorption. Co-oximeters measure the "fractional" saturation which is defined by the following equation: Fractional $SaO_2=[O_2Hb/(O_2Hb+reduced\ Hb+COHb+MetHb)] \times 100$ (Equation 6). In clinical circumstances where other Hb moieties are present, the $SpO_2$ measurement is higher than the $SaO_2$ reported by the blood gas laboratory. In most patients, MetHb and COHB are present in low concentrations so that the "functional" saturation approximates the "fractional" value.

Pulse oximetry has been utilized in all patient age groups to detect and prevent hypoxemia. The clinical benefits of pulse oximetry are enhanced by its simplicity. Modern pulse oximeters are noninvasive, continuous, and auto-calibrating. They have quick response times and their battery backup provide monitoring during transport. The clinical accuracy is typically reported to be ±2–3% at 70–100% saturation and ±3% at 50–70% saturation. Published data from numerous investigations support accuracy and precision reported by instruments manufacturers. Photographic retinal oximeters should also have similar accuracy and precision, be noninvasive and auto-calibrating.

The appropriateness of a decision to use a particular monitoring technique, pulse oximetry versus photographic retinal oximetry, necessitates an appreciation of both physiologic and technical limitations. Despite the numerous clinical benefits of pulse oximetry, other factors impact on its accuracy and reliability. Factors that are deleterious to pulse oximetry measurements include: whether the patient is anesthetized; the presence of such compounds as dyshemoglobins, vital dyes, and/or nail polish; variations and type of ambient light; LED variability (including variability due to manufacture, power supply, and so on); motion artifact; and background "noise". Electrocautery can interfere with pulse oximetry if the radio-frequency emissions are sensed by the photodetector. Reports of burns and/or pressure necrosis at the oximeter situs exist but are infrequent. These complications can be reduced by inspecting the digits during monitoring. None of these problems exist or interfere with photographic retinal oximetry.

There is overwhelming evidence supporting the capability of photographic retinal oximetry for detecting desaturation before it is clinically apparent. Photographic retinal oximetry has a wide applicability in many hospital and non-hospital settings. Some sources of error that could be apparent with photographic retinal oximetry are those that exist with pulse oximetry. A source of photographic retinal oximetry error that deserves mention is the interference caused by dyes and abnormal hemoglobins. Methylene blue, indocyanine green, and indigo carmine cause transient, apparent desaturation when administered intravenously. Methylene blue has the most profound and complex effects on $SPO_2$. It both produces and clears methemoglobin, causes a transient increase in cardiac output followed by cardiac depression, and has an absorbance peak at 668 nm that interferes with the oximeter's detection of red absorbance and indicates desaturation.

Methemoglobin can cause falsely high or low $SPO_2$ readings, depending on the relative amounts of oxyhemoglobin and reduced hemoglobin. However, as the methemoglobin level increases, the $SPO_2$ decreases to 80–85% and then remains constant.

Carboxyhemoglobin is read as approximately 90% saturated by photographic retinal oximeters. Therefore, it can cause falsely elevated $SpO_2$ readings in heavy smokers or in those with carbon monoxide poisoning if they have "true" low $SaO_2$ levels with elevated carboxyhemoglobin levels. Fetal hemoglobin has no clinically significant effect on photographic retinal oximetry.

These and other features and advantages of the invention will be more fully understood from the following description of specific embodiments of the invention taken together with the accompanying drawings.

BRIEF DESCRIPTION OF THE DRAWINGS

FIG. 3 is a tissue composite showing dynamic and static components that affect light absorption during pulse oximetry (adapted from Ohmeda 3700. Pulse Oximeter Users Manual. Madison, Wis. Ohmeda, 1989, Page 22. Provided by Ohmeda, Inc. The BOC Group);

FIG. 4 is a schematic representation of the absorption of light by living tissues. Note that the arterial blood (the ac component) is the only pulsatile component in the series of light absorbers in living tissues. The dc component represents all of the nonpulsatile absorbers (adapted from Ohmeda Pulse oximeter model 3700 Service Manual);

FIG. 5 shows oxyhemoglobin dissociation curves. The relationship between arterial saturation of hemoglobin and oxygen tension is represented by the sigmoid-shaped oxyhemoglobin dissociation curve. When the curve is left-shifted, the hemoglobin molecule binds oxygen more tightly (reproduced from Brown M, Vender J S: Non-invasive oxygen monitoring. Crit. Care Clin. 4:495, 1988);

FIG. 6 shows an experimental setup for measuring data to determine a spectrophotometric curve for glucose (reproduced from Mahadevan-Jansen, et al., "Near-Infrared Raman Spectroscopy for In Vitro Detection of Cervical Precancers", Photochemistry and Photobiology, 1998, 68(1), p. 126);

FIG. 7 shows a graph containing a spectrophotometric curve for glucose (reproduced from Mahadevan-Jansen, et al., "Near-Infrared Raman Spectroscopy for In Vitro Detection of Cervical Precancers", Photochemistry and Photobiology, 1998, 68(1), p. 126);

FIG. 8 shows a table containing data used in determining a spectrophotometric curve for glucose (reproduced from Small, et al., "Strategies for Coupling Digital Filtering with Partial Least-Squares Regression: Application to the Determination of Glucose in Plasma by Fourier Transform Near-Infrared Spectroscopy", Anal. Chem. 1993, 65, p. 3281);

FIG. 9 shows a graph containing spectrophotometric curves for glucose (reproduced from Small, et al., "Strategies for Coupling Digital Filtering with Partial Least-Squares Regression: Application to the Determination of Glucose in Plasma by Fourier Transform Near-Infrared Spectroscopy", Anal. Chem. 1993, 65, p. 3281);

FIG. 10 shows two graphs each containing spectrophotometric curves for glucose (reproduced from Small, et al., "Strategies for Coupling Digital Filtering with Partial Least-Squares Regression: Application to the Determination of Glucose in Plasma by Fourier Transform Near-Infrared Spectroscopy", Anal. Chem. 1993, 65, p. 3281);

FIG. 11 shows a graph containing spectrophotometric curves for glucose (reproduced from F. A. L'Esperance, M.D., "Ophthalmic Lasers",C.V. Mosby publisher, St. Louis, 1989, p. 68, courtesy Martin Mainster, M.D., "Laser Technology and Clinical Applications");

Corresponding reference characters indicate corresponding parts throughout the several views of the drawings.

DETAILED DESCRIPTION OF THE INVENTION

Figure 1:
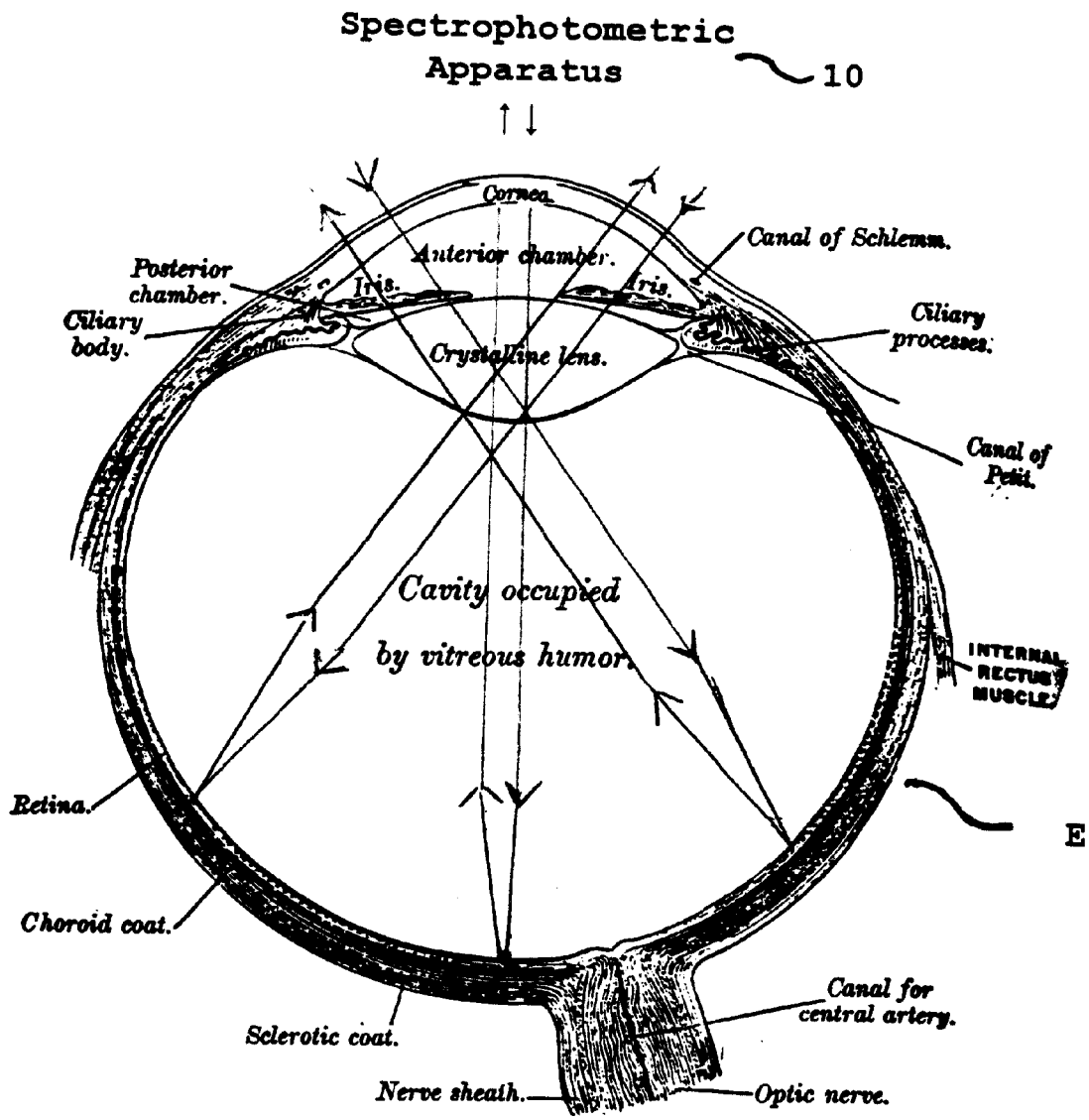
FIG. 1 is a top plan view of the spectrophotometric apparatus of the present invention shown in schematic, the instrument being shown in alignment with an eye, the eye being shown in a horizontal sectional view.

The spectrophotometric apparatus 10, 10a of the present invention is illustrated in FIG. 1 oriented relative to an eye E for non-invasively measuring the spectrophotometric absorption of one or more components of the blood in the eye. From this spectrophotometric absorption, the chemistry of the blood in the eye may be determined.

Figure 2:
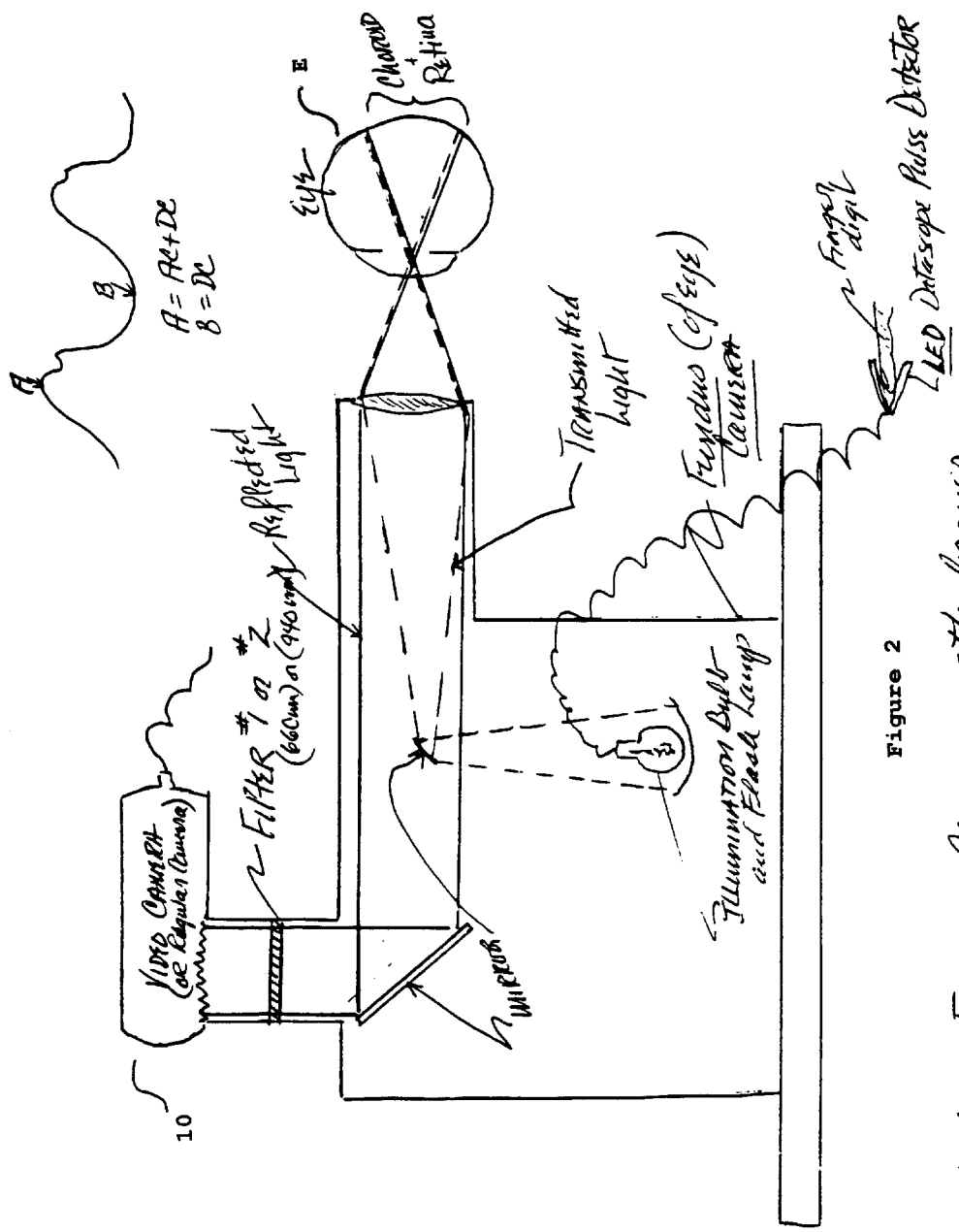
FIG. 2 is an enlarged schematic view of the spectrophotometric apparatus of FIG. 1.
Figure 12:
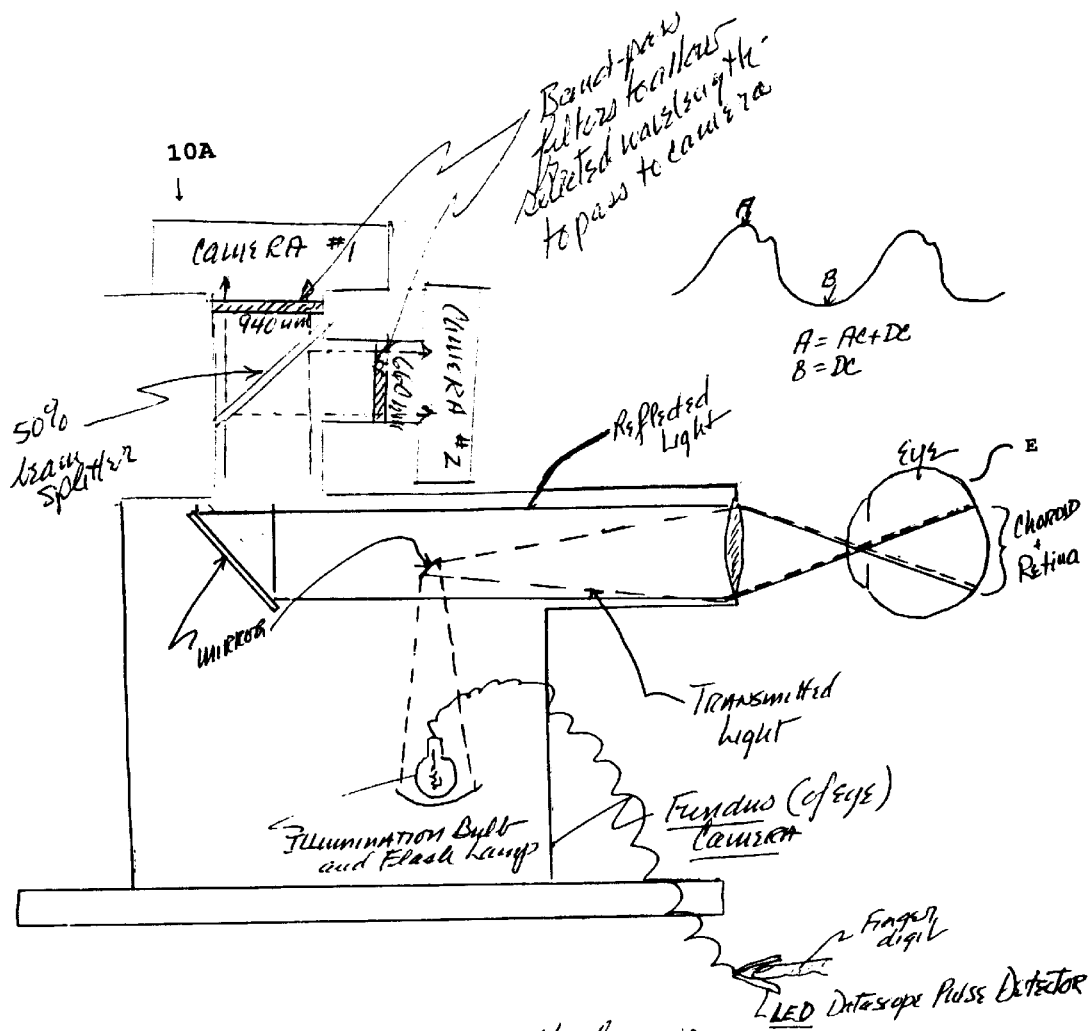
FIG. 12 is an enlarged schematic view of an alternative embodiment of the spectrophotometric apparatus of FIG. 2.
Figure 13:
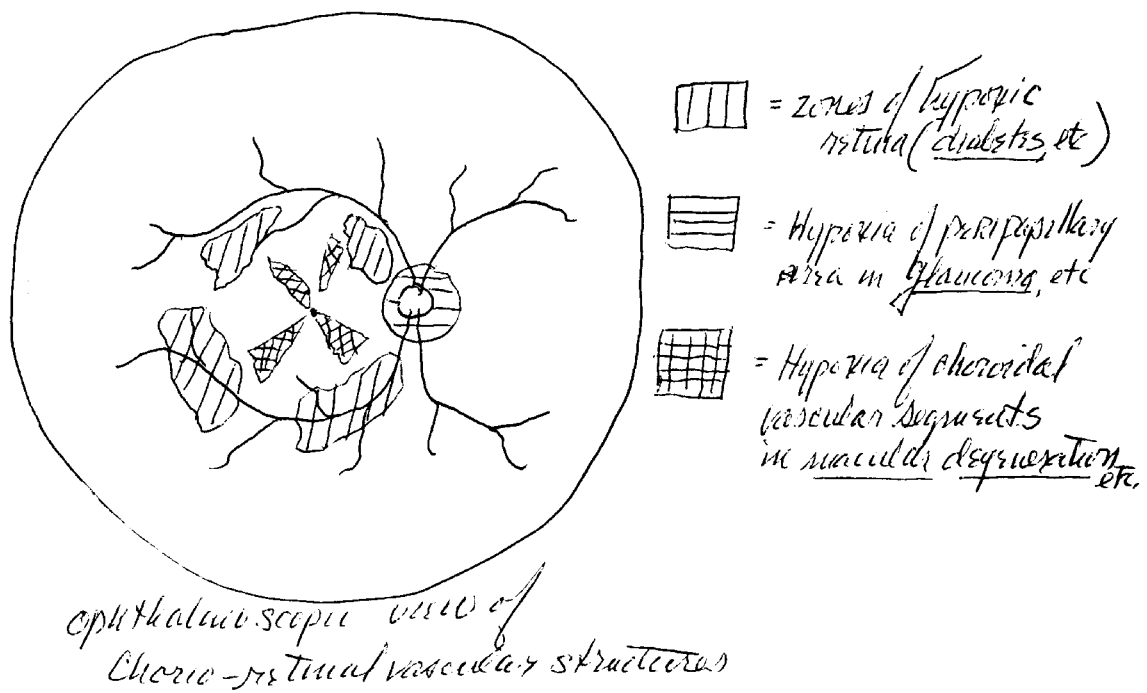
FIG. 13 is a schematic view of an image of the retina produced by the spectrophotometric apparatus of FIGS. 2 and 12.

Utilizing the Topcon 5000 Digital Ophthalmic Photography Camera, either a 35° or 50° or larger angle photograph of the retina is selected for photographic oximetry analysis. Regular color photographic images of the entire choroid and retina and/or selected portions thereof are photographed. initially. Alternatively, the photograph may be of the posterior pole of the fundus, and/or of the posterior retina and choroid. Utilizing a slightly brighter flash source, which is programmable function available for the Topcon 5000 Camera, a band-pass filter is utilized over the input port to the sensitive video camera exactly at the position where the fluorescein angiographic barrier filter normally would have been placed. In this way, the retina and choroid are illuminated with a bright flash through the dilated pupil, and the resulting spectrum of light is returned through the camera apparatus to the video camera after passing through the band-pass filter. This band-pass filter filters all light except for a narrow range around 660 nm or 940 nm, as shown in FIG. 2.

The light that has traversed through the retina and through the choroid, and has been reflected from the sclera back through the choroid and retina once again, and then through the transparent media of the eye, and through the optical system of the camera, impinges on the video camera. The purpose of the 660 nm band-pass filter is to allow only wavelengths close to 660 nm to be photographed by the video camera during the non-pulsatile phase of chorioretinal circulation; this comprises only the venous non-oxygenated blood and the non-pulsatile arteriole oxygenated blood, both of which are not in an arteriole-pulse phase during recording by the video camera. Similarly, by placing a band-pass filter narrowly grouped around 940 nm before the video camera, this filter would allow recording the absorption (and transmission) that takes place during the pulsatile phase, which would include the newly pulsed oxyhemoglobin that has flowed into the vascular bed of the choroid and retina, as well as the non-pulsatile oxyhemoglobin and reduced non-oxygenated hemoglobin noted previously. The difference between the oxygen saturation recorded at 940 nm is due to the incoming pulse phase of oxyhemoglobin and the dormant non-pulsatile oxyhemoglobin and reduced hemoglobin will determine the relative oxygenation of that portion of the choroid and retina in the eye.

For purposes of optimization, and to achieve the least error, the 660 nm photograph should be taken at the lowest portion or trough of the arteriole pulsewave, and the 940 nm photograph should be taken at the peak or crest of the pulsewave. The difference between the lowest and the highest portions of the pulsewave equals the amount of the oxyhemoglobin that has flowed into the vascular bed of the choroid and retina, and therefore, this determines a measurement of oxygen saturation according to Equation 5. Therefore, two photographs as closely together as possible, if not nearly simultaneous, must be taken during a single pulsewave, utilizing the top and the bottom of the arteriole pulse.

Taking a photograph at the top of the pulsewave as well as at the bottom of the pulsewave can be expedited by using a digital LED finger recording plethysmograph (such as manufactured by Datascope). With each pulse, the camera can be programmed to take a picture at the top of the pulsewave, and/or at the bottom of the pulsewave, in order that the photographs can be overlapped and, through the process of digital subtraction, the oxygen saturation can be determined for various parts of the choroid and sclera and optic nerve region. A plethysmograph on earlobe can also be used to determine the top and bottom of the arteriole pulsewave form, but a finger clip is preferable.

The purpose of obtaining the oxygen saturation in any portion of the choroid and retina is to determine the relative oxygen capabilities inherent in the choroid and retina. These capabilities vary considerably in patients with central or branch retinal vein occlusions, diabetic retinopathy, other vascular diseases (such as age-related macular degeneration), and other problems relating to insufficient blood supply. The determination of the status of the patient with macular degeneration or glaucoma, or arteriolosclerotic problems, can be followed from time to time as determined on an absolute basis for documenting suspected low pressure glaucoma, inadequate blood supply to the optic nerve or macular region, or areas of hypovascularity of the retina or choroid due to systemic diseases such as diabetes mellitus.

It should be appreciated that not only oxygen saturation can be determined, but the saturation or concentration of any other body or synthetic chemical that has a recognized spectro-photometric absorption curve or for which such a curve can be obtained. Blood glucose concentrations, alcohol levels, blood urea nitrogen, carbon dioxide, and any concentration of a blood constituent now determined by intravenous extraction and analysis can be measured in a non-invasive and immediate fashion using a technique similar to the photographic retinal oximetry process but utilizing the appropriate filters. In addition, the analysis of the concentration of any exogenous dyes or chemicals introduced into the body by intravenous, oral, or other route can be analyzed by the retinal and choroidal circulation. Levels of various types of drugs or medications, including legal or illegal forms of medications or drugs, can be determined by the appropriate chorioretinal photographs utilizing the appropriate band-pass filters to document the non-pulsatile (low curve), from the pulsatile phase of the pulsewave (high determination). This could have enormous potential for all types of investigative as well as analytical work with substances dissolved in the blood or carried by any of the blood components themselves.

To facilitate the use of this invention in the field, such as in doctors' offices, with emergency care providers (e.g., ambulances, remote rescue teams, etc.), it would be useful for the determination of the concentration of various substances to have a library of curves using the same technique. Thus, another aspect of this invention is a method for making a library of response curves using the techniques described above using a standard sample having a known amount of a known additive. The standard could be blood, plasma, water, or any other suitable fluid from which useful readings can be obtained. A known amount of the particular additive/drug/chemical is added to the standard and measurements are taken as described above. It may be useful to test using blood, plasma, or a simulated bodily fluid because of the interaction among the various constituents present in a living person. Likewise, it would be useful to test the metabolite of a particular additive because the pharmacology may be such that the substance is changed depending upon its mode of administration, and so the curve obtained for the metabolite compound may be different from the unmetabolized compound. Once a curve is obtained, it can be stored in a library (on any conventional digital or analog storage medium). Thereafter, the above-described technique can be used on a patient and the curve compared with those stored in the library; software programs exist for comparing curves (e.g., as a suspect's fingerprints are compared to fingerprints stored in a library). It may also be useful to use different frequencies/wavelengths/lasers to determine curves for different materials because a better separation might be found. Near-Infrared Raman Spectrosocopy for the Detection of Glucose Experimental Methods The NIR Raman spectra are measured in vitro using the system shown in FIG. 6. A 40 mW GaAl As diode laser (Diolite 800. LiCONix, Santa Clara, Calif.) is used to excite samples in a quartz cuvettes at 789 nm through a 200 $\mu$m core diameter glass optical fiber. The excitation beam is incident at an angle of approximately 70° with respect to the surface normal to avoid specular reflection and is focused with a lens to a spot size of 200 $\mu$m at the cuvette surface. The laser power at the sample is maintained at 25 mW($\pm$1%). A bandpass filter with a transmission of 85% at 789 nm ($\pm$10 nm) is used to attenuate spontaneous modes and broadband DC output of the diode laser. Spectra from the samples is measured with the bandpass filter placed after the laser but before the excitation filter.

The scattered Raman signal is collected at an angle of 90° from the excitation beam and imaged at the entrance slit of the detection system. The detection system consists of an imaging spectrograph (500IS, Chromex Inc. Albuquerque, N.Mex.) and a liquid nitrogen cooled charge coupled device camera (LN-1152E, Princeton Instruments, Trenton, N.J.). The spectrograph is used with a 300 grooves/mm grating, blazed at 500 nm. This grating along with an entrance slit of 100 $\mu$m, yields a spectral resolution of 10 cm$^-$. A holographic notch filter (HSNF 789 nm is used to attenuate the elastic scattering, Raman spectra are measured from 500 to 2000 cm$^-$relative to the excitation frequency.

A background spectrum is acquired prior to each sample scan using the same parameters as used for tissue scans with a blank cuvette as sample. The resultant spectrum is then subtracted from each sample spectrum. In addition, each background subtracted spectrum is corrected for wavelength dependent response of the spectrograph, camera, grating and filters. The system is calibrated daily for wavenumber and throughput variations using naphthalene, rhodamine 6G and carbon tetrachloride. The measured Raman shift is found to be accurate to ±7 cm$^{-1}$ and the calibrated intensity is accurate to ±12% of the mean.

Spectra have been measured from chromophores that could potentially contribute to tissue Raman scattering. They were collagen, elastin, NADH, FAD, glucose, glycogen, glucose 1-phosphate, hemoglobin, nucleic acids, tryptophan, tyrosine and various phospholipids. These chromophores were obtained commercially (Sigma Inc., St. Louis, Mo.) and spectra were measured in their pure powdered form, contained in a quartz cuvette.

Results

The Raman spectrum of a dilute solution of glucose following fluorescence subtraction and noise smoothing is shown in FIG. 7. Comparison of the measured glucose Raman spectrum with published Raman spectra (see for example, glucose spectrum in Small et al. indicates that the glucose spectra are similar (±8 cm$^{-1}$) in the region of 600–1800 cm$^{-1}$.

The entire disclosures of the following are expressly incorporated by reference herein:

Ohmeda 3700, Pulse Oximeter Users Manual. Madison, Wis., Ohmeda, Inc., The BOC Group, 1989;

Brown M, Vender J S: Non-invasive oxygen monitoring. Crit. Care Clin. 4:495, 1988;

Mahadevan-Jansen, et al., "Near-Infrared Raman Spectroscopy for In Vitro Detection of Cervical Precancers", Photochemistry and Photobiology, 1998, 68(1), p. 123 to 132);

Small, et al., "Strategies for Coupling Digital Filtering with Partial Least-Squares Regression: Application to the Determination of Glucose in Plasma by Fourier Transform Near-Infrared Spectroscopy", Anal. Chem. 1993, 65, p. 3279 to 3289; and F. A. L'Esperance, M.D., "Ophthalmic Lasers", C.V. Mosby publisher, St. Louis, 1989.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A method for spectrophotometric measurement of the concentration of a selected component in the blood flow in the choroid and retinal vascular structures of the eye, said method comprising:

determining the characteristic spectrophotometric absorption curve of the selected component, the characteristic spectrophotometric absorption curve including, but not limited to, the wavelength of the electromagnetic spectrum most highly absorbed by the selected component;

directing a source of electromagnetic spectrum containing one or more wavelengths through the cornea of the eye to the chorio-retinal vascular structures within the eye;

measuring the intensity of the single or multiple analytical wavelengths directed through the cornea;

measuring the intensity of the analytical wavelength(s) emerging from the chorio-retinal vascular structures and exiting the eye through the cornea;

subtracting the intensity of the analytical wavelength(s) emerging from the chorio-retinal vascular structures from the intensity of the analytical wavelength(s) directed toward the cornea to determine the portion of the analytical wavelength(s) absorbed by the blood in the chorio-retinal vascular structures; and calculating the concentration of the selected component in the blood in the chorio-retinal vascular structure based on the portion of the analytical wavelength(s) absorbed by the blood in the chorio-retinal vascular structures.

2. A method as set forth in claim 1, and further comprising the step of providing a sensor for said detecting of the intensity of the analytical wavelength emerging from the chorio-retinal vascular structures, the sensor being positioned relative to the eye such that the sensor and the electromagnetic source face the same surface of the chorio-retinal vascular structures wherein the analytical wavelength, after passing through the retina and choroid in that sequence, is reflected from the sclera back through the chorio-retinal vascular structures toward the sensor.

3. A method as set forth in claim 1, and further comprising the step of positioning the electromagnetic spectrum source relative to the eye such that the analytical wavelength(s) is directed through the cornea, retina and choroid, the analytical wavelength(s) upon exiting the choroid striking the sclera and being reflected by the sclera so as to be directed back through the choroid, retina, and cornea, the method further comprising the step of providing a sensor positioned relative to the eye such that the analytical wavelength(s) upon exiting the cornea is received by the sensor wherein the sensor detects the intensity of the analytical wavelength (s) emerging from the chorio-retinal vascular structures.

4. A method as set forth in claim 1 wherein said directing step comprises directing toward the eye an electromagnetic spectrum source which emits one or more rays having an analytical wavelength, such that each ray is directed to a selected location on the retina, said measuring step for the analytical wavelength directed through the cornea comprising measuring the intensity of the ray(s), said measuring step for the analytical wavelength emerging from the chorio-retinal vascular structures comprising measuring the intensity of the ray(s), said calculating step comprising calculating the concentration of the selected component in the blood in the chorio-retinal vascular structures based on the intensity of the ray(s) emerging from the chorio-retinal vascular structures, said calculating step further comprising correlating the calculated concentration (s) with the selected location(s) on the retina.

5. A method as set forth in claim 4 wherein said directing step comprises emitting a plurality of rays, said calculating step comprising calculating the concentrations corresponding to each of the rays, said calculating step further comprising correlating the calculated concentrations with the selected locations on the retina to form a coherent image of the retina.

6. A method as set forth in claim 1, wherein said determining step comprises determining the characteristic spectrophotometric absorption curves for oxyhemoglobin and reduced hemoglobin, said calculating step comprising calculating the concentration of oxygen in the blood in the chorio-retinal vascular structures based on the concentration of oxyhemoglobin and reduced hemoglobin in the blood in the chorio-retinal vascular structures using single or multiple analytical wavelengths of light delivered in a simultaneous or sequential manner.

7. A method as set forth in claim 1 wherein said determining step comprises determining the analytical wavelengths of oxyhemoglobin and reduced hemoglobin, said measuring step for the analytical wavelengths directed through the cornea comprising measuring the intensity of each of the analytical wavelengths, said measuring step for the analytical wavelengths emerging from the chorio-retinal vascular structures comprising measuring the intensity of each of the analytical wavelengths, said calculating step comprising calculating the concentration of oxygen in the blood in the chorio-retinal vascular structures based on the intensity of the analytical wavelengths for oxyhemoglobin and reduced hemoglobin emerging from the chorio-retinal vascular structures.

8. A method as set forth in claim 1, wherein said determining step comprises determining the characteristic spectrophotometric absorption curve for glucose, said calculating step comprising calculating the concentration of a glucose in the blood in the chorio-retinal vascular structures using single or multiple analytical wavelengths of light delivered in a simultaneous or sequential manner.

9. A method as set forth in claim 1 wherein said determining step comprises determining the analytical wavelength of glucose, said calculating step comprising calculating the concentration of glucose in the blood in the chorio-retinal vascular structures based on the intensity of the analytical wavelength for glucose emerging from the chorio-retinal vascular structures.

10. A spectrophotometric apparatus for the eye comprising:

a source for emitting electromagnetic spectrum having at least one analytical wavelength, said electromagnetic spectrum source including a source detector for sensing the intensity of the analytical wavelength emitted from said electromagnetic spectrum source;

a base for fixing the orientation of said electromagnetic spectrum source relative to the eye to direct the electromagnetic spectrum emitted from the source through the cornea of the eye to the choriod and vascular structures within the eye; and a receiver detector for sensing the intensity of the analytical wavelength emerging from the chorio-retinal vascular structures and exiting the eye through the cornea, said receiver detector being mounted on said base, said base enabling fixing of the orientation of said receiver detector relative to the eye.

11. A spectrophotometric apparatus as set forth in claim 10, and further comprising a pulse actuator electrically connected to said receiver detector, said pulse actuator having means for sensing the pulse of blood circulation of a patient, said pulse actuator having further means for operating said receiver detector to measure the intensity of the analytical wavelength at a predetermined time during the pulse of the blood.

12. A spectrophotometric apparatus as set forth in claim 11, wherein said pulse actuator operates said receiver detector to measure the intensity of the analytical wavelength when the pulse of the blood is maximum.

13. A spectrophotometric apparatus as set forth in claim 11, wherein said pulse actuator operates said receiver detector to measure the intensity of the analytical wavelength when the pulse of the blood is minimum.

14. A spectrophotometric apparatus as set forth in claim 10, wherein said electromagnetic spectrum source emits a plurality of analytical wavelengths, said receiver detector defining a first receiver detector for sensing a first analytical wavelength, said instrument further comprising:

a second receiver detector for sensing a second analytical wavelength, said second receiver detector being mounted on said base; and a beam splitter for directing the analytical wavelengths emerging from the chorio-retinal vascular structures to said first and second receiver detectors, said beam splitter being mounted on said base.

15. A spectrophotometric apparatus as set forth in claim 14, and further comprising a pulse actuator electrically connected to said first and second receiver detectors, said pulse actuator being able to sense the pulse of blood circulation of a patient, said pulse actuator being further able to operate said first and second receiver detectors to measure the intensity of the analytical wavelengths at a predetermined time relative to the pulse of the blood.

16. A spectrophotometric apparatus as set forth in claim 15, wherein said pulse actuator effectuates said operation of said first and second receiver detectors during the same predetermined time relative to the pulse of the blood.

17. A spectrophotometric apparatus as set forth in claim 15, wherein said pulse actuator effectuates said operation of said first and second receiver detectors during different predetermined times relative to the pulse of the blood.

18. A spectrophotometric apparatus as set forth in claim 10, said receiver detector defining a first receiver detector for sensing an analytical wavelength, said instrument further comprising:

a second receiver detector for sensing the analytical wavelength, said second receiver detector being mounted on said base;

a beam splitter for directing the analytical wavelength emerging from the chorio-retinal vascular structures to said first and second receiver detectors, said beam splitter being mounted on said base; and a pulse actuator electrically connected to said first and second receiver detectors, said pulse actuator being able to sense the pulse of blood circulation of a patient, said pulse actuator being further able to operate said first and second receiver detectors to measure the intensity of the analytical wavelengths at respective first and second predetermined times relative to the pulse of the blood.

19. A spectrophotometric apparatus as set forth in claim 18, wherein said first predetermined time is when the pulse of the blood is maximum, said second predetermined time is when the pulse of the blood is minimum.

20. A spectrophotometric apparatus as set forth in claim 10, and further comprising a filter mounted on said base, said filter being located between said receiver detector and the eye such that the electromagnetic spectrum emerging from the chorio-retinal vascular structures passes through said filter and to said receiver detector, said filter being transparent to the analytical wavelength and opaque to all other wavelengths.

21. A spectrophotometric apparatus as set forth in claim 20, and further comprising:

a translator mounted on said base, said translator able to move said filter into and out of said location between said receiver detector and the eye;

a pulse actuator electrically connected to said translator, said pulse actuator able to sense the pulse of blood circulation of a patient, said pulse actuator further able to operate said translator to cause said filter to move to said location at a first predetermined time relative to the pulse of the blood enabling said receiver detector to measure the intensity of the analytical wavelength.

22. A spectrophotometric apparatus as set forth in claim 20, wherein said receiver detector comprises a camera mounted on said base.

23. A spectrophotometric apparatus as set forth in claim 10, and further comprising:
a video camera electrically connected to said receiver detector such that said video camera receives a signal from said receiver detector indicating the intensity of the characteristic wavelength emerging from the chorio-retinal vascular structures.

24. A spectrophotometric apparatus as set forth in claim 10, wherein said receiver detector comprises a photoelectric cell.

25. A spectrophotometric apparatus as set forth in claim 10, wherein said receiver detector comprises a photodiode.

26. A spectrophotometric apparatus as set forth in claim 10, wherein said electromagnetic spectrum source emits wavelengths within the limits of transmittance of the cornea and lens of the eye.

27. A spectrophotometric apparatus as set forth in claim 10, wherein said electromagnetic spectrum source emits wavelengths between 400 nm and 8 microns.

28. A spectrophotometric apparatus as set forth in claim 10, wherein said receiver detector comprises a video camera for detecting electromagnetic energy, principally in the ultraviolet, visible, infrared, and microwave region of that spectrum, emerging from the cornea, after transversing the choroid and retina and reflecting back from the sclera, in such a way to form a photographic-like image or picture.

29. A spectrophotometric apparatus as set forth in claim 10, wherein said receiver detector comprises regular photographic film or a digital array camera.

30. A spectrophotometric apparatus as set forth in claim 10, wherein said receiver detector comprises a regular photon or energy detector.

31. A spectrophotometric apparatus for an eye comprising:
an emitting wavelength source for directing energy into the eye;
an appropriate detector to record and analyze a single ray of electromagnetic energy or multiple rays of energy exiting the eye, said detector organizing the energy in such a way as to form an image or picture correlating the energy to a specific location on the eye such that the energy can be analyzed as a whole; and
a pulse actuator electrically connected to said detector, said pulse actuator having means for sensing the pulse of blood circulation of a patient, said pulse actuator having further means for operating said detector for said recording of said single ray or multiple rays of energy exiting the eye at a predetermined time during the pulse of the blood.

32. A spectrophotometric instrument for the eye comprising:
a source for emitting electromagnetic spectrum containing at least one analytical wavelength, said electromagnetic spectrum source including a source detector for sensing the intensity of the analytical wavelength emitted from said electromagnetic spectrum source;
a base for being hand-held by the user, said base being able to direct the electromagnetic spectrum emitted from said source through the cornea of the eye to the choroid and vascular structures within the eye; and
a receiver detector mounted on said base, said receiver detector being able to sense the intensity of the analytical wavelength emerging from the chorio-retinal vascular structures and exiting the eye through the cornea, said base enabling orientation of said receiver detector relative to the eye such that, when said electromagnetic spectrum source is positioned for directing the light emitted therefrom through the cornea of the eye, said receiver detector is oriented relative to the eye for sensing the intensity of the analytical wavelength emerging from the chorio-retinal vascular structures.

\* \* \* \* \*